United States Patent [19]

McMullen et al.

[11] 4,410,715

[45] Oct. 18, 1983

[54] PROCESS FOR THE EPOXIDATION OF OLEFINS USING A GROUP V METAL CO-CATALYST I AND A PHENOLIC HYDROCARBON CO-CATALYST II

[75] Inventors: Charles H. McMullen, Allendale, N.J.; Eugene E. Fehskens, Suffern; Jeffrey S. Plotkin, Monsey, both of N.Y.

[73] Assignee: Exxon Research & Engineering Co., Florham Park, N.J.

[21] Appl. No.: 398,086

[22] Filed: Jul. 14, 1982

[51] Int. Cl.³ ........................................... C07D 301/12
[52] U.S. Cl. .................................................... 549/531
[58] Field of Search ........................................ 549/531

[56] References Cited

U.S. PATENT DOCUMENTS 3,993,673 11/1976 McMullen .......................... 549/531
4,286,068 8/1981 Mares et al. ........................ 549/531

FOREIGN PATENT DOCUMENTS 8496 3/1980 European Pat. Off. .
9262 4/1980 European Pat. Off. .
2803757 8/1978 Fed. Rep. of Germany ...... 549/531
754359 8/1956 United Kingdom .
1143433 2/1969 United Kingdom .
1302441 1/1973 United Kingdom .
1324763 7/1973 United Kingdom .
1399639 7/1975 United Kingdom .
1452730 10/1976 United Kingdom .

OTHER PUBLICATIONS

Jacobson et al., Jour. Am. Chem. Soc. (1979), vol. 101 (23), pp. 6946–6950, "Biphase and Triphase Catalysis. Arsonated Polystyrenes as Catalysts for Epoxidation of Olefins by Aqeuous Hydrogen Peroxide".

M. Pralus et al., Fundamental Research in Homogeneous Catalysis, vol. 3 (1979) edited by M. Tsutsui, Plenum Press, pp. 327–343.

Primary Examiner—Norma S. Milestone
Attorney, Agent, or Firm—Robert A. Maggio

[57] ABSTRACT

A process for epoxidizing olefins with hydrogen peroxide in the presence of a catalyst composition comprising a Group V element containing Co-catalyst I, such as diphenylarsinic acid, and a phenol containing compound having a $pK_a$ of from about 5 to about 13 as Co-catalyst II such as p-chlorophenol is disclosed.

13 Claims, No Drawings

PROCESS FOR THE EPOXIDATION OF OLEFINS USING A GROUP V METAL CO-CATALYST I AND A PHENOLIC HYDROCARBON CO-CATALYST II

BACKGROUND OF THE INVENTION

This invention relates to a process and catalyst composition for the epoxidation of olefins by hydrogen peroxide.

The epoxides constitute a class of compounds of which the industrial importance is measured by the tonnages produced and by the diversity of their applications in the field of urethanes, glycols, surface-active agents, plasticizers and numerous other derivatives.

While many specific methods for epoxidizing olefins are known, the most prominent of these methods can generally be divided into four basic types. For example, the oldest industrial technique for the epoxidation of double bonds is the process known as the chlorohydrin process. In the chlorohydrin process an olefin is reacted with chlorine in an alkaline medium. The yields (based on the chlorine) are unsatisfactory. This process also gives rise to the simultaneous formation of considerable quantities of chlorinated by-products, both inorganic and organic, which products are unsuitable for any known purpose. The disposal of these by-products involves problems of such magnitude that this process may eventually be abandoned.

The second type of epoxidation method is generally limited to the epoxidation of ethylene. In accordance with this method ethylene is epoxidized with good yields in the vapor phase by means of molecular oxygen over a catalyst on a silver base. However, this technique is not very useful for the higher carbon olefins because of its lack of selectivity.

A third and more recent type of epoxidation process is characterized by the use of organic hydroperoxides. In accordance with processes of this type an olefin is epoxidized catalytically in an organic medium containing an organic hydroperoxide oxidant. In addition to employing a relatively expensive organic hydroperoxide as an oxidant, it is also a characteristic disadvantage of these processes that the epoxide formation is accompanied by the formation in an equivalent or even greater amount of an alcohol derived from the organic hydroperoxide employed in the process. Consequently, the commercial viability of these processes is always influenced by the ability to economically dispose of the alcohol by-product in addition to the epoxide.

Accordingly, new methods of access to the olefin oxides have been sought which are more direct, more selective, and especially are free from the problem of byproducts.

This has led to the development of the fourth type of epoxidation process which is characterized by the use of hydrogen peroxide as the oxidant.

Hydrogen peroxide is in principle a desirable reagent, for the very reason of its oxidizing non-polluting nature. However its reactivity towards olefins is weak or non-existent in the absence of an activating agent which enables a more active peroxy compound to be formed in-situ. Different processes of epoxidation have therefore been proposed using, for example, organic peracids such as performic, peracetic or perpropionic acids (see, for example, Belgium Pat. No. 535,068). Nevertheless, because of the instability of the epoxides in acid medium, such processes are particularly difficult to put into practice.

It has been proposed to use oxides, oxyacids, or peroxyacids derived from metals such as arsenic, antimony, bismuth, and tungsten (see for example U.S. Pat. No. 3,993,673, European Patent Application Publication Nos. 0 008 496 and 0 009 262; and British Pat. No. 754,359). However, when such metal catalysts are employed in conjunction with aqueous hydrogen peroxide, the hydrogen peroxide is either rapidly decomposed or the rate of epoxidation is uneconomical. Thus, in an aqueous medium the addition of a metallic catalyst can be self-defeating. Consequently, for optimum performance when using these catalysts an important requirement of the system is that the hydrogen peroxide be anhydrous. However economic mass production of hydrogen peroxide has become possible owing to developments in the oxidation of secondary alcohols or quinone compounds. These routes to hydrogen peroxide synthesis as practiced commercially ultimately produce dilute aqueous solutions of hydrogen peroxide. Consequently, the cheapest commercially available hydrogen peroxide is generally sold as a 35-40% by weight, aqueous solution thereof. If one has to remove the water from these solutions for use in anhydrous sytems, the effective cost of the hydrogen peroxide is increased substantially, thereby increasing the cost of any system requiring the use of anhydrous hydrogen peroxide. It would therefore be economically beneficial to develop a catalytic system which can operate in a medium containing sufficient water such that commercially available aqueous solutions of hydrogen peroxide could be used directly without concentration and/or purification.

U.S. Pat. No. 3,778,451 discloses the epoxidation of olefins in an organic solvent medium containing hydrogen peroxide, transition metal compounds, i.e., those of molybdenum, tungsten, vanadium, niobium, tantalum, uranium or rhenium, and a nitrogenous organic base. The organic solvent employed includes alcohols, glycols, esters, linear or cyclic ethers, and certain weak carboxylic acids. However the hydrogen peroxide is employed in substantially anhydrous and concentrated form e.g. contains less than 10%, preferably less than 1% water to limit the production of undesirable hydroxylated by-products.

British Pat. No. 1,399,639 discloses the use of a fluorinated ketone, e.g., hexafluoroacetone, or hydrate thereof as a catalyst which can be used in excess quantities to function also as a solvent, or hexafluoroisopropanol (HFIP) as the solvent. However, this patent does not disclose the use of the phenolic Co-catalyst II of the present invention nor does it disclose the use of any catalyst in conjunction with the specific Group V element containing co-catalysts disclosed herein. Moreover, a majority of reaction times disclosed therein range from about 4 to as high as 270 hours, generally between 5 and 18 hours.

Similarly, it has been reported that the reaction product of hexafluoroacetone with concentrated hydrogen peroxide, i.e., 2-hydroperoxy-hexafluoro-2-propanol, in combination with 30% to 90% $H_2O_2$ (latter gives best results) provides for the catalytic epoxidation of alkenes (see R. P. Heggs, JACS, 2484-2486, 1979). Later, the same Journal reported on arsenated polystyrenes as catalysts for the epoxidation of olefins by aqueous hydrogen peroxide (Jacobson et al, JACS 6946-6950, 1979).

U.S. Pat. No. 4,024,165 discloses that the olefin epoxidation process with hydrogen peroxide can be carried out in a fluorinated alcoholic solvent in which all the reactants and catalysts are soluble by using as the catalyst composition a soluble transition metal compound (the disclosed transition metals being limited to molybdenum, tungsten, vanadium, niobium, tantalum, uranium, or rhenium) and a soluble nitrogen-containing compound. In this patent the hydrogen peroxide is present as an aqueous solution, usually 50% by weight (see column 3, lines 19–27). However, the reaction times reported in this reference associated with yields of any significance of olefin oxide range from about 5 to about 8 hours. At reaction times below about 5 hours, the yield of olefin oxide drops substantially and in some instances no reaction at all takes place. Moreover, when either the transition metal compound or the nitrogen containing compound is eliminated from the catalyst composition, yields of olefin oxide also drop significantly. (Compare Examples 1 and 2 wherein Example 2, elimination of the nitrogen containing compound results in the undesirable polymerization of the olefin oxide; compare also Examples 21 and 24 wherein elimination of the transition metal compound in Example 24 drops the yield from 70 to 35%).

U.S. Pat. No. 4,257,948 discloses a process for epoxidizing acyclic, cyclic, or polycyclic olefins using hydrogen peroxide and a hexachloroacetone catalyst. This patent does not disclose the use of any transition metal catalysts or any other catalyst.

U.S. Pat. No. 3,993,673 discloses a process for epoxidizing olefins in the presence of an arsenic catalyst essentially free of tungsten, molybdenum, vanadium and chromium, a hydrogen peroxide oxidant, and an inert organic solvent. Suitable organic solvents include ethers, esters, alcohols, glycols, chlorinated solvents including chlorinated hydrocarbons, and chlorinated aromatics (e.g., chlorobenzene, o-dichlorobenzene, chloroform, and 1,1,2,2-tetra chloro ethane). Although the "hydrogen peroxide can be used in aqueous solutions . . . it is preferred to use less water than more" (column 3, lines 43–47). Such chlorinated solvents are not disclosed in this reference to possess any catalytic activity, nor do any of the disclosed chlorinated materials include the phenolic co-catalysts of the present invention.

European patent application Publication No. 0 008 496 discloses a polymer supported arsenic heterogeneous catalyst and a process for using the same to oxidize ketones, esters, and olefins in the presence of hydrogen peroxide. When dilute aqueous solutions of hydrogen peroxide are employed as the oxidant, a water immiscible solvent must be employed to avoid contact and hydrolysis of the oxidation products with water. In this embodiment, the substrate to be oxidized as well as the oxidation product are dissolved in the water immiscible solvent creating a two phase organic/aqueous system wherein the hydrogen peroxide is present in the aqueous phase. The polymer supported arsenic catalyst, functioning as a phase transfer catalyst, concentrates at the phase boundary whereat the arsono groups in the polymer are converted by contact with the hydrogen peroxide to perarsono, and this group on contacting the compound to be oxidized in the organic phase oxidizes it with regeneration of the arsono group. Thus, while suitable water immiscible solvents are disclosed as including chlorinated hydrocarbons, such as chloroform, these solvents are employed solely for their water immiscible property and not for any promoting effect on the arsenic catalyst.

Other phase transfer catalytic systems are disclosed in U.S. Pat. No. 3,992,432 and British Pat. No. 1,324,763.

European patent application Publication No. 0 009 262 discloses the in-situ production of hydrogen peroxide and use of the resulting hydrogen peroxide directly in arsenic catalyzed epoxidation reactions of olefins. The in-situ production of hydrogen peroxide as well as the epoxidation reaction can be conducted in the presence of aliphatic or cycloaliphatic ethers, aliphatic esters, chlorinated alkanes, chlorinated arenes or sulfolane. None of the solvents disclosed include the phenolic Co-catalysts II of the present invention.

British Patent Specification No. 1,452,730 discloses a process for epoxidizing olefins using acetic acid as the catalyst in the presence of aqueous hydrogen peroxide and an inert, chlorinated aliphatic hydrocarbon solvent such as chloroform. The solvent limits the hydrolysis of epoxidized products by the aqueous $H_2O_2$/acetic acid solution. Although, the exact mechanism by which this is achieved is not disclosed, it is known that the chlorinated hydrocarbon solvents are water immiscible. Consequently, it is believed that these solvents shield, to varying degrees, the epoxidized product from contact with the aqueous phase by solubilizing the epoxidized product therein. The phenolic Co-catalyst II of the present invention is not dependent on water immiscibility for its promoting effect, and in fact is generally water miscible due to the polar hydroxy group.

Other patents which disclose acid catalysis include U.S. Pat. No. 3,248,404 (discloses aliphatic and aromatic mono carboxylic acids and their halogenated derivatives as catalysts, e.g., acetic acid, chloroacetic acid, and benzoic acid in conjunction with a sequestering agent having acid complex forming properties); British Pat. No. 1,143,433 (discloses a carboxylic acid cation exchange resin as a catalyst); U.S. Pat. No. 2,870,171 (discloses the use of a tungsten acid deposited on an inert support as catalyst); and British Patent Specification No. 754,359 (discloses the use of inorganic peracids catalysts such as the peracids of tungsten, vanadium, and molybdenum as well as heteropoly acids such as the heteropolytungstic acids of arsenic, antimony or bismuth).

British Pat. No. 1,302,441 is directed to a process for epoxidizing olefins using hydrogen peroxide and a two component catalyst composition comprising as a first component an organo tin compound having at least one hydroxyl group or coordination group which can be converted to a hydroxyl group in the presence of water or hydrogen peroxide, and as a second component, at least one compound containing at least one of molybdenum, tungsten, vanadium, selenium, and boron. Suitable solvents for the reaction include alcohols, e.g., straight chain alcohols, polyhydric alcohols, and cyclic alcohols, as well as epoxides, ketones, and furfurals. Halogenated solvents are not disclosed. While this patent does not require the use of anhydrous or substantially anhydrous hydrogen peroxide, it will be noted that when aqueous solutions of hydrogen peroxide are employed, the reaction times vary from 4 to 24 hours. For example, at 90% concentrations of $H_2O_2$ in water (Examples 1, 2 and 4–14) the average reaction time is about 13 hours. However at 70% $H_2O_2$ in water (Examples 15–18) the reaction time is always 20 hours. In contrast when no water is employed with the $H_2O_2$ (Examples 35–52) reaction times are measured in minutes (e.g. 60 to 360 minutes). Thus, the activity of the catalyst composition of this patent is reduced substantially even at relatively high $H_2O_2$ concentrations in water.

Further, it was reported in the Chemical and Engineering news issue of December 11, 1978 on page 24 that both Produits Chemique Ugine Kuhlmann and Union Carbide have each directly oxidized propylene with hydrogen peroxide using an arsenic catalyst. In the former process, hydrogen peroxide of a 70% concentration is employed and for the latter 90% concentration (the author notes that the latter catalyst is adversely affected by the presence of water), with no mention of whether any additional inert diluent or solvent is present.

In summary, substantially all of the disclosures on the epoxidations of olefins to olefin epoxides, particularly propylene to propylene oxide, in which aqueous hydrogen peroxide is used directly in contact with the olefin in either the presence or absence of transition metal catalysts, have eluded commercial development due to one or more economic disadvantages. For example, the aqueous hydrogen peroxide used typically must be substantially above 30% in concentration, and/or the selectivity to propylene oxide is low, or the amount of time required for the reaction is too long. For these reasons, a practical route for direct epoxidation of olefins by aqueous hydrogen peroxide is a long-standing goal in oxidation chemistry. More specifically, it would be extremely economically advantageous to provide a process for epoxidizing olefins using extremely short reaction times while simultaneously achieving comparable or better yields obtainable with prior art techniques particularly, in a dilute aqueous system of $H_2O_2$. Extremely short reaction times enable one to employ simpler plant designs by drastically reducing the size of the reaction vessel. Extremely short reaction times also permit one to employ simplified product separation techniques, such as conventional product flash-off procedures, wherein product is continually vaporized directly from the reaction medium, recovered and isolated. If the reaction time is too long, the amount of product vaporized at any given time would be too small to make this technique economically feasible. The ability to use dilute aqueous solutions of $H_2O_2$ would further increase the flexibility and improve the economics of the process.

Accordingly, there has been a continuing search for processes and catalyst compositions that permit the use of dilute aqueous $H_2O_2$ containing reaction mixtures, where it is advantageous to do so, and which substantially reduce the epoxidation reaction time without sacrificing olefin oxide yield to the point where the process becomes uneconomical.

One response to this search is provided in commonly assigned U.S. patent application Ser. No. 387,341, filed June 11, 1982, of M. G. Romanelli, which is directed to a process for epoxidizing olefins with hydrogen peroxide in the presence of a catalyst composition comprising as a Co-catalyst I, at least one Group V element containing compound, said Group V element being selected from As, P, Sb, and Bi (e.g., phenyl arsonic acid), and as a Co-catalyst II at least one fluorinated compound containing an oxygenated functional group such as hexafluoroisopropanol. The scope of the fluorinated oxygenated compounds disclosed in this application, however, is limited to those compounds wherein the oxygenated functional group is located on a saturated aliphatic carbon and not an aromatic carbon. While the invention disclosed in this application represents a substantial improvement over the aforedescribed prior art vis-a-vis the rate and/or selectivity of the epoxidation reaction, particularly when employing the hydrogen peroxide as a commercially available dilute aqueous solution, there has been a further continuing search for alternative compounds which can perform the same function of these Co-catalyst II fluorinated oxygenated compounds but which are more readily available commercially at a substantially lower cost. The present invention was developed in response to this search also.

SUMMARY OF THE INVENTION

In one aspect of the present invention there is provided a process for reacting at least one olefinic compound having at least one ethylenic unsaturation with $H_2O_2$, in the presence of a catalyst composition in a manner and under conditions sufficient to oxidize at least one of said ethylenically unsaturated groups to its corresponding epoxide group. The catalyst composition capable of catalyzing the epoxidation of olefins with $H_2O_2$ comprises at least one Co-catalyst I and at least one Co-catalyst II. The composition of each Co-catalyst is described hereinafter in detail.

DESCRIPTION OF THE PREFERRED EMBODIMENTS

The present invention is directed to catalyst compositions and processes for using the same to epoxidize olefins with hydrogen peroxide.

More specifically, the catalyst composition comprises at least one Group V element or Group V element-containing compound collectively referred to herein as Co-catalyst I and at least one phenolic, preferably halogenated phenolic, hydrocarbon compound referred to herein as Co-catalyst II.

The Group V element of Co-catalyst I is selected from the group consisting of As, P, Sb, and Bi. Co-catalyst I comprises inorganic and organic derivative compounds of the Group V elements as well as the elements themselves.

Co-catalyst I is believed to exert its catalytic effect by reacting with hydrogen peroxide in-situ to form a catalytic intermediate species having, under reaction conditions, an oxidation potential greater than the oxidation potential of hydrogen peroxide alone. The term oxidation potential as used herein is defined to be the potential of a substance to oxidize the ethylenic unsaturation of the olefinic compound to its corresponding epoxide. However, the aforedescribed intermediate species is believed to be in equilibrium with the $H_2O_2$ and Co-catalyst I from which it is formed. Co-catalyst II, in some yet undetermined manner, is believed to facilitate the formation of this intermediate species even in the presence of water, by activating Co-catalyst I. This activated Co-catalyst I is believed to possess a greater propensity to react with the $H_2O_2$ to form the intermediate species and therefore shifts the equilibrium reaction which forms said intermediate species in the forward direction. Consequently, the particular identity of the Co-catalyst I compound selected for use in the present invention is dictated and controlled by its possession of the capability of interacting with hydrogen peroxide to form said intermediate species under reaction conditions. Typical of such compounds which possess this capability are those which possess an oxy acid functionality or those which can form an oxy acid functionality in-situ. An oxy acid functionality possesses at least one oxo (i.e. o=) group and at least one hydroxy group attached to the aforedescribed Group V element such as

wherein M represents a Group V metal as described herein. In short, Co-catalyst I appears to catalyze the oxidation of the olefin by hydrogen peroxide through the formation of an intermediate, and Co-catalyst II appears to catalyze the formation of the intermediate.

The following is a representative description of Co-catalyst I compounds which are believed to be capable of forming said intermediate with hydrogen peroxide although this description is not intended to be exhaustive.

Accordingly, inorganic Co-catalyst I Group V element containing compounds include inorganic: oxides, acids such as oxy acids, oxy acid salts, halides, oxy halides, thio halides, sulfides, oxy sulfides and metalides.

Representative inorganic oxides include $As_2O_3$, $As_2O_5$, $P_4O_6$, $P_4O_8$, $P_4O_9$, $P_4O_{10}$, $Sb_4O_6$, $Sb_2O_4$, $Sb_4O_6$, $SbO_2$, $Bi_2O_3$, $5Bi_2O_3.3UO_3$, $2As_2O_3.12H_2O$ and mixtures thereof.

Representative inorganic oxy acids include $H_2[HPO_3]$, $H_3PO_4$, $H_4P_2O_7$, $H_3PO_2$, $As(OH)_3$, $H_3AsO_4$, $Bi(OH)_3$, and $Sb_2O_3.(H_2O)_n$.

Representative oxy acid salts include the alkali metal (e.g., Li, Na, K, Rb, Cs), alkaline earth metal (e.g., Be, Mg, Ca, Sr, Ba), ammonium and tetrahydrocarbyl ammonium, preferably tetra lower alkyl (e.g., $C_1$ to $C_{10}$ alkyl) ammonium, salts of the aforenoted oxy acids, including $NaH_2PO_4$, $Na_2HPO_4$, $KH_2AsO_4$, $K[Sb(OH)_6]$, $NaBiO_3$, $Na_3AsO_4$, tetra ethyl ammonium dihydrogen phosphate, tetra methyl ammonium dihydrogen arsenate, ammonium dihydrogen arsenate and mixtures thereof.

Representative halides and oxy halides include those represented by the structural formulae $PX_3$, $P_2X_4$, $X_3PO$, $X_3PS$, $X_2(O)—P—O—P—(O)—X_2$, $P(H)_a(X)_b$ wherein X is at least one halide independently selected from the group consisting of Cl, F, Br, I, and a+b is 5, including such compounds as for example $P_2Cl_4$, $P_2I_4$, $PHF_4$, $PH_2F_3$, $PH_4Cl$, $PCl_3$, $PCl_5$, $Cl_3PS$, $PF_5$; those represented by the structural formulae $MX_3$ and $MX_5$ where M is As, Sb or Bi, and X is at least one halide as defined above, including such compounds as for example: $AsCl_3$, $AsF_3$, $BiCl_3$, $SbF_3$, $SbCl_3$, $AsF_5$, $SbF_5$, $SbCl_5$, $SbCl_3F_2$, $SbCl_2F_3$, $SbCl_4F$; those represented by the structural formula MOX wherein M and X are defined above including such compounds as for example: SbOCl, BiOCL, and AsOCl; $KSb_2F_7$, and $As_2I_4$.

Representative thio halides include: SbSCl, AsSCl, BiSF, $AsSCl_3$ and mixtures thereof.

Representative sulfides and oxy sulfides include: $As_2S_3$, $As_2S_5$, $BiOS_2$, $Sb_2OS_2$ and mixtures thereof.

Representative examples of suitable metalides include: $As_2Zn_3$, $5Bi_2O_3.3VO_3$, $2As_2O_3.12H_2O$ and mixtures thereof.

The most preferred inorganic Co-catalyst I compounds are those containing As as the Group V element, most preferably the As oxides.

Organic Co-catalyst I compounds include those represented by the structural formulae: $R_1ZX'Y$, $R_1R_2ZX'$, and $R_1R_2R_3Z$, wherein: Z is a Group V element in the plus 3 oxidation state selected from the group consisting of P, As, Sb, and Bi; $R_1$, $R_2$ and $R_3$ which may be the same or different are selected from the group of hydrocarbyl radicals consisting of: alkyl, typically alkyl of from about 1 to about 20, preferably from about 1 to about 10, and most preferably from about 1 to about 5 carbons; aryl, typically aryl of from about 6 to about 14, preferably from about 6 to about 10, and most preferably 6 carbons; alkoxy, aryloxy, alkoxyaryl, aryloxyalkyl, aralkyl, alkylthio, arylthio, and alkaryl, wherein the alkyl and aryl groups thereof are as described immediately above in connection with alkyl and aryl respectively; cycloalkyl, typically cycloalkyl of from about 4 to about 20, preferably from about 5 to about 15, and most preferably from about 6 to about 10 carbons; or any two of said $R_1$, $R_2$, and $R_3$ groups together can constitute a cyclic hydrocarbon group having a carbon number as described for cycloalkyl immediately above; substituted: alkyl, aryl, cycloalkyl, alkoxy, aryloxy, alkoxyaryl, aryloxyalkyl, alkylthio, arylthio, alkaryl, or aralkyl, wherein said substituents are selected from the group consisting of: halogen (i.e., Cl, F, Br, I, most preferably F) and nitro, and mixtures thereof; and X' and Y which may be the same or different are selected from the group consisting of: hydrogen; halogen (i.e., Cl, F, Br, I), hydroxy, alkyl, aryl, alkaryl, and aralkyl, said groups being defined as above respectively in connection with $R_1$ to $R_3$; alkoxy wherein the alkyl group thereof is as defined above in connection with $R_1$ to $R_3$; acyloxy

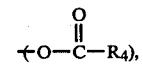

mercapto (—SH), alkylthio (—$SR_5$) and thioacyloxy

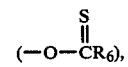

wherein $R_4$, $R_5$, and $R_6$ are alkyl as defined in connection with $R_1$ to $R_3$.

Representative examples of suitable compounds falling within the scope of the above structural formulae are provided below in chart form wherein each of the variable groups are associated in specific compounds. In the following exemplification, the inclusion of a substituent in parenthesis indicates it can be substituted on any position in the hydrocarbyl group to which it is attached.

| | FORMULA: $R_1ZX'Y$ | | |
|---|---|---|---|
| $R_1$ | Z | X' | Y |
| $C_5H_{11}—$ | As | —H | —H |
| $C_6H_5—$ | As | —Cl | —Cl |
| $C_5H_{11}O—$ | As | —F | —F |
| $C_6H_5O—$ | P | —Br | —Br |
| $CH_3—\phi—$ | P | —I | —I |
| $\phi—CH_2—O—$ | P | —OH | —OH |
| $(Cl)C_5H_{10}—$ | Sb | —$C_5H_{11}$ | —$C_5H_{11}$ |
| $(F)C_5H_{10}—$ | Sb | —$C_6H_5$ | —$C_6H_5$ |
| $(Br)C_5H_{10}—$ | Sb | $CH_3—\phi$ | $CH_3—\phi$ |
| $(I)C_5H_{10}—$ | Bi | $C_5H_{11}O—$ | $C_5H_{11}O—$ |
| $(NO_2)C_5H_{10}—$ | Bi | $\overset{O}{\underset{\|}{—OC}}—C_5H_{11}$ | $\overset{O}{\underset{\|}{—OC}}—C_3H_7$ |
| $(C_3H_7O)C_5H_{10}—$ | Bi | —SH | —SH |

-continued

| FORMULA: $R_1ZX'Y$ | | | |
|---|---|---|---|
| $R_1$ | Z | X' | Y |
| $(C_3H_7S)C_5H_{10}-$ | As | $-SC_3H_7$ | $-SC_3H_7$ |
| $C_6H_5S-$ | P | $-OCC_3H_7$ (S double bond) | $-OS-C_3H_7$ (O double bond) |

$\phi$ = Phenyl

| FORMULA: $R_1R_2ZX'$ | | | |
|---|---|---|---|
| $R_1$ | $R_2$ | Z | X' |
| $C_5H_{11}-$ | $C_6H_5-$ | As | $-H$ |
| $C_6H_5-$ | $C_5H_{11}O-$ | P | $-Cl$ |
| $C_5H_{11}O-$ | $C_6H_5O-$ | Bi | $-F$ |
| $C_6H_5O-$ | $C_6H_5O-$ | Sb | $-Br$ |
| $CH_3-\phi-$ | $CH_3-\phi-$ | As | $-I$ |
| $\phi-CH_2O-$ | $\phi-CH_2O-$ | P | $-OH$ |
| $CH_3-\phi-O-$ | $CH_3-\phi-O-$ | As | $-OH$ |
| $(Cl)C_5H_{10}-$ | $(Cl)C_5H_{10}-$ | Bi | $-C_5H_{11}$ |
| $(F)C_5H_{10}-$ | $(F)C_5H_{10}-$ | Bi | $-C_6H_5$ |
| $(Br)C_5H_{10}-$ | $(Br)C_5H_{10}-$ | Sb | $-\phi-CH_3$ |
| $(I)C_5H_{10}$ | $(I)C_5H_{10}$ | As | $C_5H_{11}O-$ |
| $(NO_2)C_5H_{10}-$ | $(NO_2)C_5H_{10}-$ | As | $-OC-C_5H_{11}$ (O double bond) |
| $(C_3H_7O)C_5H_{10}-$ | $(C_3H_7O)C_5H_{10}-$ | P | $-SH$ |
| $(C_3H_7S)C_5H_{10}-$ | $(C_3H_7O)C_5H_{10}$ | P | $-SC_3H_7$ |
| $C_6H_5S-$ | $C_6H_5S-$ | Bi | $-OC-C_3H_7$ (S double bond) |
| (cyclic)* | | As | $-OH$ |
| $C_6H_5-$ | $C_6H_5$ | As | Cl |

*$R_1$ and $R_2$ together constitute a cyclic hydrocarbon

| FORMULA: $R_1R_2R_3Z$ | | | |
|---|---|---|---|
| $R_1$ | $R_2$ | $R_3$ | Z |
| $C_5H_{11}-$ | $CH_3-$ | $CH_3-$ | As |
| $C_6H_5-$ | $C_6H_5-$ | $C_5H_{11}$ | P |
| $C_5H_{11}O-$ | $C_5H_{11}O-$ | $C_5H_{11}O-$ | Bi |
| $C_6H_5O-$ | $C_6H_5O-$ | $C_5H_{11}O-$ | Sb |
| $CH_3-\phi-$ | $CH_3-\phi-$ | $C_5H_{11}-$ | Bi |
| $\phi-CH_2-$ | $\phi-CH_2-$ | $\phi-CH_2-$ | P |
| $(Cl)C_5H_{10}-$ | $(Cl)C_5H_{10}-$ | $CH_3-$ | As |
| $(F)C_5H_{10}-$ | $CH_3-$ | $CH_3-$ | P |
| $(Br)C_5H_{10}$ | $CH_3-$ | $CH_3-$ | Bi |
| $(I)C_5H_{10}-$ | $C_6H_5O-$ | $CH_3-$ | Sb |
| $(NO_2)C_5H_{10}-$ | $CH_3-$ | $CH_3-$ | Bi |
| $(C_3H_7O)C_5H_{10}-$ | $C_2H_5-$ | $C_2H_5O-$ | P |
| $(C_3H_7S)C_5H_{10}-$ | $CH_3-$ | $CH_3-$ | As |
| $C_6H_5S-$ | $C_2H_5-$ | $C_2H_5-$ | P |
| $C_6H_5-$ | $C_6H_5-$ | $C_6H_5-$ | As |

Another class of Group V element containing organic compounds are those in which the Group V element, represented by $Z_1$ hereinbelow, is in the plus 5 oxidation state. Such compounds include those represented by the structural formulae $R_1Z_1(O)X'Y$, $R_1R_2Z_1(O)X'$, and $R_1R_2R_3Z_1(O)$ wherein $R_1$, $R_2$, $R_3$, $X'$ and Y are as defined above in connection with the aforenoted structural formulae wherein the Group V element is in the plus 3 oxidation state.

The preferred Group V element containing organic Co-catalyst I compounds are those of the structural formulae $R_1Z_1(O)X'Y$ wherein $X'$ and Y are hydroxyl and $R_1$ is a halogen substituted, preferably fluorine substituted for unsubstituted hydrocarbyl group selected from alkyl, aryl, aralkyl, alkoxyaryl, most preferably aryl, said hydrocarbyl groups being as defined in connection with $R_1$ above; and $R_1R_2Z_1(O)X'$ wherein $R_2$ is as described in connection with $R_1$ immediately above, and $R_1$, Z, and $X'$ also are as described immediately above.

Also included within the scope of Co-catalyst I are polymers wherein the Group V element is located in a group pendant to the polymer backbone. A representative example of such a polymeric Co-catalyst I is illustrated by the structural formula:

$$CA_3-[CA_2-CA]_n-CA_3$$
$$(R_1)_{\overline{a'}}-Z_1(O)(OH)_2$$

wherein $Z_1$ is as described above, A is independently selected from hydrogen and halogen, preferably fluorine, $R_1$ is a hydrocarbyl group selected from alkyl, and aryl said hydrocarbyl groups being as defined in connection with $R_1$ above, (a') is a number of 0 or 1, and n is a number which can vary from about 5 to 1000, preferably 5 to 500.

Representative compounds falling within the scope of the above formulae for Co-catalyst I are described below wherein each of the variable groups are associated in specific compounds.

| FORMULA: $R_1Z_1(O)X'Y$ | | | |
|---|---|---|---|
| $R_1$ | $Z_1$ | X' | Y |
| $C_5H_{11}-$ | As | $-H$ | $-OH$ |
| $C_6H_5-$ | As | $-Cl$ | $-OH$ |
| $C_5H_{11}O-$ | As | $-F$ | $-H$ |
| $C_6H_5O-$ | P | $-Br$ | $-Br$ |
| $CH_3-\phi-O-$ | P | $-I$ | $-OH$ |
| $CH_3-\phi-$ | P | $-OH$ | $-OH$ |
| $(Cl)C_5H_{10}-$ | Bi | $-C_5H_{11}$ | $-C_5H_{11}$ |
| $(F)C_5H_{10}-$ | Bi | $-C_6H_5$ | $-C_5H_{11}$ |
| $(Br)C_5H_{10}-$ | Bi | $\phi-CH_2-$ | $-C_2H_5$ |
| $(I)C_5H_{10}-$ | Sb | $C_5H_{11}O-$ | $C_5H_{11}O-$ |
| $(NO_2)C_5H_{10}-$ | Sb | $-OC-C_5H_{11}$ (O double bond) | $-OC-C_5H_{11}$ (O double bond) |
| $(C_3H_7O)C_5H_{10}-$ | Sb | $-SH$ | $-SH$ |
| $(C_3H_7S)C_5H_{10}-$ | As | $-SC_3H_7$ | $-SC_3H_7$ |
| $C_6H_5S-$ | As | $-OC-C_3H_7$ (S double bond) | $-OC-C_3H_7$ (S double bond) |
| $CH_3-CH_2-\phi-$ | As | $-OH$ | $-OH$ |
| $CF_3-CF_2-\phi-$ | As | $-OH$ | $-OH$ |
| $CH_3-CH_2-C_6H_3F-$ | As | $-OH$ | $-OH$ |
| $CF_3-CF_2-C_6H_2F_2-$ | As | $-OH$ | $-OH$ |
| $C_6H_4F-$ | As | $-OH$ | $-OH$ |
| $C_6H_3F_2-$ | As | $-OH$ | $-OH$ |
| $(NO_2)-C_6H_4-$ | As | $-OH$ | $-OH$ |
| $C_6H_3Cl_2-$ | As | $-OH$ | $-OH$ |
| $CH_3O-C_6H_4-$ | As | $-OH$ | $-OH$ |
| $CH_3-(CH_2)_{\overline{n}}$ | As | $-OH$ | $-OH$ |
| $CF_3-(CF_2)_{\overline{n}}$ | As | $-OH$ | $-OH$ |
| $\phi-(CH_2)_{\overline{n}}$ | As | $-OH$ | $-OH$ |
| $C_6H_3F_2-$ | As | $-OH$ | $-OH$ |
| $C_6H_4F-$ | As | $-OH$ | $-OH$ |
| $C_6H_5-$ | As | $-OH$ | $-OH$ |
| $C_3H_7-$ | As | $-OH$ | $-OH$ |
| $C_6H_5$ | Sb | $-OH$ | $-OH$ |

FORMULA: $R_1R_2Z_1(O)X'$

-continued

| $R_1$ | $R_2$ | $Z_1$ | X' |
|---|---|---|---|
| $C_5H_{11}-$ | $C_5H_{11}-$ | As | $-OH$ |
| $C_6H_5-$ | $C_6H_5-$ | As | $-OH$ |
| $C_5H_{11}O-$ | $C_5H_{11}O-$ | As | $-Br$ |
| $C_3H_7-$ | $C_3H_7O-$ | P | $-H$ |
| $CH_3-\phi-$ | $CH_3-\phi-$ | P | $-OH$ |
| $(Cl)C_5H_{10}-$ | $(Cl)C_5H_{10}-$ | P | $-OH$ |
| $C_5Cl_{11}-$ | $C_5Cl_{11}-$ | Bi | $C_5H_{11}-$ |
| $C_5F_{11}-$ | $C_5F_{11}-$ | Bi | $C_5H_{11}-$ |
| $(NO_2)C_5H_{10}-$ | $(NO_2)C_5H_{10}-$ | Bi | $-C_2H_5$ |
| $C_6H_4F-$ | $C_6H_4F-$ | Sb | $C_5H_{10}O-$ |
| $C_5H_{11}\overset{O}{\underset{\parallel}{C}}-O-$ | $C_5H_{11}\overset{O}{\underset{\parallel}{C}}-O-$ | As | $\overset{O}{\underset{\parallel}{-OC}}-C_5H_{11}$ |
| $C_3H_7-$ | $C_3H_7-$ | Sb | $-SH$ |
| $C_6H_5-$ | $C_6H_5-$ | As | $-SC_3H_7$ |
| $C_3H_7-$ | $C_6H_5-$ | Bi | $-SC_3H_7$ |
| $CH_3-$ | $CH_3-$ | As | $-OH$ |
| $CH_3-CH_2-\phi-$ | $CH_3-CH_2-\phi-$ | As | $-OH$ |
| $CH_3-CH_2-C_6H_3F-$ | $CH_3-CH_2-C_6H_3F-$ | As | $-OH$ |
| $CF_3-CF_2-C_6H_2F_2-$ | $CF_3-CF_2-C_6H_2F_2-$ | As | $-OH$ |
| $C_6H_4F-$ | $C_6H_4F-$ | As | $-OH$ |
| $C_6H_3F_2-$ | $C_6H_3F-$ | As | $-OH$ |
| $(NO_2)-C_6H_4-$ | $(NO_2)-C_6H_4-$ | As | $-OH$ |
| $C_6H_3Cl-$ | $C_6H_3Cl-$ | As | $-OH$ |
| $CH_3-O-C_6H_2$ | $CH_3-O-C_6H_4-$ | As | $-OH$ |
| $C_6H_5-$ | $C_6H_5-$ | Sb | OH |

FORMULA: $R_1R_2R_3Z_1(O)$

| $R_1$ | $R_2$ | $R_3$ | $Z_1$ |
|---|---|---|---|
| $C_5H_{11}-$ | $C_5H_{11}-$ | $C_5H_{11}-$ | As |
| $C_6H_5-$ | $C_6H_5-$ | $C_6H_5-$ | As |
| $C_6H_5O-$ | $C_6H_5O-$ | $C_6H_5O-$ | As |
| $C_6H_5-$ | $CH_3$ | $CH_3$ | Sb |
| $C_6H_4F-$ | $C_6H_4F-$ | $C_6H_4F-$ | Bi |
| $NO_2C_5H_{10}-$ | $C_6H_5-$ | P | |
| $CH_3CH_2-$ | $CH_3CH_2-$ | $CH_3CH_2-$ | As |

FORMULA: $CA_3\text{-}CA_2CA\text{-}_{\overline{n}}\text{-}CA_3$
$(R_1)_{\overline{a'}}-Z_1(O)(OH)_2$

| A | $R_1$ | a' | $Z_1$ |
|---|---|---|---|
| H— | N/A | 0 | As |
| H— | $-C_6H_4-$ | 1 | As |
| H— | $-CH_2-$ | 1 | As |
| F— | N/A | 0 | As |
| F— | $-C_6H_4-$ | 1 | As |
| F— | $-CH_2-$ | 1 | As |
| H— | $-C_6H_4-$ | 1 | P |
| F— | $-C_6H_4-$ | 1 | P |
| H— | $-CH_2-$ | 1 | Bi |
| F— | $-CH_2-$ | 1 | Bi |
| H— | $-C_6H_4-$ | 1 | Sb |
| F— | $-CH_2-$ | 1 | Sb |

Also included as suitable Co-catalyst I are those having at least two of the aforedescribed Group V elements such as 1-diphenyl-phosphino-2-diphenyl arsinoethane and 2-arsenato-ethyl-triphenyl phosphonium bromide.

The preferred class of organic Group V element containing compounds include the arsenic containing compounds. Of this class, the most preferred organic compounds include: arsenic triethoxide, phenylarsonic acid, diphenylarsinic acid, dimethylarsinic acid, 2-nitro-4-methylphenylarsonic acid, 4-methylphenylarsonic acid, n-propyl arsonic acid, 4-hydroxy-3-nitrophenyl arsonic acid and mixtures thereof.

Co-catalyst II is selected on the basis of its $pK_a$, its possession of a phenolic functionality and its oxidative stability. The $pK_a$ of a compound is a conventional term and as used herein it represents the value of $-\text{Log } K_a$ where $K_a$ is the dissociation or ionization constant of the Co-catalyst as determined in aqueous solution at 25° C.

Accordingly, it has been found that Co-catalysts II suitable for use in the present invention must possess a $pK_a$ of typically from about 5 to about 13, preferably from about 6 to about 11, and most preferably from about 7 to about 10.

Generally, the lower the $pK_a$ of Co-catalyst II, the higher will be the acidity of the phenolic hydroxy group and its associated co-catalytic activity. However, if the $pK_a$ of the Co-catalyst II is below about 5 it will be sufficiently acidic to cause unacceptable competing side reactions such as ring opening of the epoxide product. While compounds with such a low $pK_a$ may be effective to impart co-catalytic activity, they deleteriously affect the overall yield of epoxide, and hence can be self-defeating for the ultimate purpose for which they are employed.

If the $pK_a$ of the compound employed as Co-catalyst II is above about 13, (e.g. 2-propanol), it will not possess sufficient co-catalytic activity for the purpose of the present invention.

A further preferred requirement of the Co-catalyst II is that it be sufficiently oxidatively stable under reaction conditions such that it is not oxidized to any significant extent by the $H_2O_2$ during epoxidation reaction. Oxidation of Co-catalyst II not only wastefully consumes $H_2O_2$, but more importantly it also destroys or substantially reduces co-catalytic activity.

While unsubstituted phenols possess a suitable $pK_a$ of about 9.9 and exhibit good co-catalytic activity, they generally also exhibit poor oxidative stability and will eventually be oxidized to hydroxy or polyhydroxy benzenes under reaction conditions. One of the benefits of employing a Co-catalyst II which does not participate directly in the epoxidation reaction, is that it can be continuously recycled without the addition of new Co-catalyst. Consequently, this benefit, to a large degree, will be lost if unsubstituted phenols are employed as Co-catalyst II and consumed by the oxidant. Thus, while unsubstituted phenols can be employed where economics of the process permit, it is preferred to employ phenols substituted with substituents capable of stabilizing and/or controlling the $pK_a$ of, the phenol parent compound as described herein.

Inert electron withdrawing substituents, such as halogens (most preferably Cl), are preferred because they not only lower the $pK_a$ of the phenol but they also increase its oxidative stability. However, oxidative stability can also be imparted by replacing the reactive hydrogens of the aromatic ring with inert hydrocarbyl and other groups described herein. As a general rule, the fewer reactive hydrogens on the aromatic ring the greater will be the oxidative stability of the phenolic compound.

Thus, the co-catalysts II of the present invention provide a delicate balance between oxidative stability, high co-catalytic activity, negligible competing side reactions, and relatively low cost, and by appropriately selecting the substituents and/or $pK_a$ of the phenolic Co-catalyst II, one is able to tailor the catalytic composition to achieve optimum performance from both a process and economic standpoint.

Co-catalyst II can therefore be broadly defined to comprise an organic, preferably completely organic compound having the aforedescribed $pK_a$ values and at least one hydroxy group substituted on an aromatic ring.

Accordingly, suitable Co-catalysts II can be represented by the structural formula:

$$(X)_a\text{—(Ar)—}(OH)_b \qquad (I)$$

wherein Ar represents a substituted or unsubstituted aromatic hydrocarbyl group, typically an aromatic hydrocarbyl group having from about 6 to about 14 carbons, preferably from about 6 to about 10 carbons, and most preferably about 6 carbons, exclusive of substituents, said substituents when present being selected from the group consisting of alkyl, typically alkyl of from about 1 to about 20, preferably from about 1 to about 10, and most preferably from about 1 to about 5 carbons, hydroxy alkyl wherein the alkyl group is as defined above, halogenated alkyl wherein the alkyl group is as defined immediately above and the halogen is as defined below in connection with X, nitro alkyl, alkoxy alkyl, aralkoxy, oxo substituted alkyl, and alkoxy carbonyl, wherein the respective alkyl and aryl groups are as described immediately above; X is selected from the group consisting halogen (i.e. F, Cl, Br and I, preferably Cl and Br, most preferably Cl), hydrogen, and nitro, preferably at least one X is halogen; the letter "a" represents a number of typically 0 to 5, preferably 1 to 4 most preferably 2 to 4, the letter "b" is a number of at least 1, typically from about 1 to about 4, preferably 1 to about 3, most preferably from about 1 to 2 (e.g. 1), the sum of a+b is equal to the total number of available carbon bonding sites, i.e., the number of replaceable aromatic hydrogens, on the Ar substituted or unsubstituted aromatic hydrocarbyl group.

Preferably X is halogen and when halogen, is preferably located on the ortho or para position of the Ar aromatic hydrocarbyl group.

A narrower more preferred class of Co-catalyst II compounds can be represented by the structural formula:

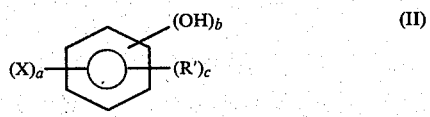

$$(II)$$

wherein R' is independently selected from the group consisting of alkyl of from about 1 to about 5; preferably 1 to about 3, most preferably 1 to about 2 carbons, and alkoxy wherein the alkyl portion thereof is as described above; c is a number of from about 0 to about 5, preferably 1 to 5, (e.g., 1 to 4) X, a and b are as described above in connection with structural formula I; and the sum of a+b+c is equal to the total number of available carbon bonding sites on the aromatic ring.

The most preferred Co-catalysts II is represented by structural formula II wherein X is chlorine, "b" is 1, "c" is 0, and "a" is from 1 to 5, typically 1 to 4, preferably 1 to 3, e.g., 1 to 2.

Representative examples of suitable Co-catalysts II include p-chlorophenol, o-chlorophenol, m-chlorophenol, 2,4-dichloro phenol, 2,6-dichlorophenol, 2,4,6-trichlorophenol, 2,3-dichlorophenol, pentachlorophenol, pentafluorophenol, p-cresol, phenol, 2,3,5-trimethylphenol, 2-methoxyphenol, o-nitrophenol, p-nitrophenol 2,4-dinitrophenol, 2,4-di-t-butylphenol, o-fluorophenol, m-fluorophenol, p-fluorophenol, 2,4-di bromophenol, 2,6-diiodophenol, 1-nitro-4-chlorophenol, 2,6-diethoxyphenol, 2,4,6-trifluorophenol, pentamethylphenol pentaethylphenol.

Preferred Co-catalysts II include p-chlorophenol, 2,4-dichlorophenol, p-nitrophenol.

In addition to the above described Co-catalysts II compounds, it is also contemplated that polymers having hydroxy groups pendant from an aromatic ring, such as hydroxylated polystyrene, may also be employed.

The Co-catalysts I and/or II may be employed in the present invention alone or in association with a heterogeneous support or carrier. Suitable supports, typically employed in powder, spherical, tablet, or cylindrical form, for the co-catalysts include, for example, silica; alumina; silica-alumina; metal aluminates, such as magnesium aluminate, calcium aluminate, titania, zirconia, activated carbon, zeolites, magnesium oxide, and basic ion-exchange resins.

When mixtures of Co-catalysts II are employed, it is the $pK_a$ of each component within the mixture which is determinative of suitability of that component for use in the present invention.

Co-catalysts I and II are employed to enhance the epoxidation reaction rate of olefins and/or selectivity to epoxide, said epoxidation reaction being achieved using $H_2O_2$ as the oxidant.

Accordingly, olefins which can be epoxidized using $H_2O_2$ and which can be employed in the present invention contain at least one ethylenic unsaturation and are conventional in the art. Typical of such olefins are those represented by the structural formula:

$$(XIV)$$

wherein $R_7$, $R_8$, $R_9$ and $R_{10}$, which may be the same or different, are selected from the group consisting of hydrogen; substituted or unsubstituted: alkyl, aryl, alkaryl, and aralkyl hydrocarbyl groups, said hydrocarbyl groups being preferably as defined in connection with R of structural formula I; or any two of said $R_7$ to $10$ groups together can constitute a cycloalkyl group typically of from about 4 to about 12, preferably from about 5 to about 8 carbons.

Representative olefins which can be epoxidized and contain at least one ethylenic saturation include: ethylene, propylene, butene-1, butene-2, isobutene, pentene-1, pentene-2, isobutene, pentene-1, pentene-2, hexene, isohexene, heptene, 3-methylhexene, octene-1, isooctene, nonene, decene, dodecene, tridecene, pentadecene, octadecene, eicosene, docosene, tricosene, tetracosene, pentacosene, butadiene, pentadiene, hexadiene, octadiene, decadiene, tridecadiene, eicosadiene, tetracosadiene, cyclopentene, cyclohexene, cycloheptene, methylcyclohexene, isopropylcyclohexene, butylcyclohexene, octylcyclohexene, dodecyclohexene, acrolein, acrylic acid, methyl methacrylate, styrene, cholestrol etc. The preferred olefins are propylene, soybean oil, isobutylene, styrene, allyl alcohol and allyl chloride. The most preferred olefin is propylene.

The components in the catalyst composition of the present invention are employed in amounts effective to increase yields and/or selectivities of epoxide relative to the absence of said components, typically within a reaction time of from about 2 minutes to about 5 hours, preferably from about 2 minutes to about 2 hours and most preferably from about 2 minutes to about 1 hour.

The process of the present invention is conducted by contacting at least one olefin containing at least one ethylenic unsaturation and $H_2O_2$, preferably in a liquid phase, in the presence of said catalyst composition under conditions and in a manner sufficient to oxidize at least one of said ethylenically unsaturated groups to its corresponding epoxide group.

The $H_2O_2$ can be employed in anhydrous form or as an aqueous solution. Such aqueous solutions typically will contain from about 3 to about 99.9%, preferably from about 20 to about 75%, and most preferably from about 20 to about 45% (e.g., 25 to 35%), by weight, $H_2O_2$ based on the total weight of the aqueous solution. While it is generally recognized in the art that yields of epoxide product are highest if the water content of the reaction mixture is kept to a minimum, it is a particular advantage of the present invention that reaction rate enhancement and yields are not particularly adversely affected when operating at water levels in the aqueous $H_2O_2$ solution of about 60 to 75% (e.g., 70%) by weight thereof including water produced by the reaction.

Consequently, the economics of the overall process are substantially increased due to the ability to use commercially produced aqueous solutions of $H_2O_2$ directly, without the need to concentrate such solutions by removing water therefrom.

While it is generally desirable to employ the reactants (i.e., olefin and $H_2O_2$) in approximately stoichiometric proportions, e.g., one mole of $H_2O_2$ per mole of ethylenic linkage to be epoxidized, an excess of either reactant is acceptable and in many instances preferable since it actually results in easier process control and a more economic process.

The preferred mode of reacting the olefin and $H_2O_2$ is conducted in a liquid reaction medium and preferably in the presence of a solvent miscible with both reactants. While it is not necessary that the reaction medium exist as a homogeneous phase, it is preferred that it does.

Because the Co-catalyst II can be used in excess relative to the effective catalytic amount, it can function not only as a Co-catalyst but also as the primary solvent for the reaction medium when employed in such excess to achieve a homogeneous liquid reaction phase. However, it may be more economically advantageous to employ less expensive solvents for this purpose.

Suitable optional solvents are organic, and inert in the reaction mixture. By inert as used herein in conjunction with optional solvents is meant that the solvent does not deleteriously affect the epoxidation reaction relative to its absence, and does not increase the formation of non-epoxidized products. Such optional inert organic solvents include aromatic hydrocarbons such as benzene, toluene, xylene, benzonitrile, nitrobenzene, adiponitrile, anisole, phenyl nonane; saturated aliphatic hydrocarbons having from about 5 to about 20 carbons, such as pentane, hexane, heptane adiponitrile; halogenated hydrocarbons such as 1,2-dichloroethane, chloroform, carbon tetrachloride and the like; non-fluorinated substituted saturated aliphatic and/or aromatic hydrocarbons having from 1 to about 20 carbons including those selected from the group consisting of alcohols such as: methanol, propanol, butanol isopropanol, 2,4-di-t-butyl phenol; ketones such as acetone; carboxylic acids such as propanoic acid, acetic acid; esters such as ethyl acetate, ethyl benzoate, dimethyl succinate, butyl acetate, tri-n-butyl phosphate; dimethyl phthalate; and ethers, such as tetraglyme; and mixtures thereof.

Preferred solvents include benzene, toluene, ethyl acetate, ethyl benzoate, dimethyl succinate, dimethyl phthalate, tetraglyme, nitrobenzene, benzonitrile, and mixtures thereof.

In carrying out a preferred embodiment of the invention, olefin or olefin and $H_2O_2$ are introduced into a liquid reaction mixture comprising Co-catalyst I, Co-catalyst II and optionally an inert organic solvent. Preferably the reaction mixture also contains an aqueous solution of the $H_2O_2$ prior to introducing the olefin thereto.

Thus, the initial preferred reaction mixture prior to olefin introduction will typically comprise: (a) an aqueous $H_2O_2$ solution (as defined above) in an amount of from about 0.5 to 25%, preferably from about 2 to about 20%, and most preferably from about 5 to about 15%, by weight, based on the weight of the reaction mixture exclusive of the weight of olefin and Co-catalyst I; (b) Co-catalyst II in an amount of from about 10 to about 99.5%, preferably from about 30 to about 90%, and most preferably from about 70 to about 90%, by weight, based on the weight of the reaction medium exclusive of the weight of olefin and Co-catalyst I; (c) inert organic solvent in an amount of from about 0 to about 90%, preferably from about 0 to about 50%, and most preferably from about 10 to about 30%, by weight, based on the weight of the reaction medium exclusive of the weight of olefin and Co-catalyst I; and (d) Co-catalyst I in an amount sufficient to achieve from about 0.001 to about 2, preferably from about 0.005 to about 1.0, and most preferably from about 0.01 to about 1.0 g atom of the Group V element in Co-catalyst I per liter of reaction medium inclusive of components (a) through (c) recited above.

If the aqueous solution of $H_2O_2$ is added simultaneously with the olefin, it is added in amounts sufficient to eventually achieve the reaction mixture composition as described above.

The olefin is introduced into, and contacted with, the reaction mixture in an amount and in a manner sufficient to achieve at least an initial molar ratio of olefin to $H_2O_2$ therein of typically from about 0.8:1 to about 50:1, preferably from about 1:1 to about 30:1, and most preferably from about 1:1 to about 10:1. Thus, in most instances it is preferred to maintain an excess of olefin in the reaction mixture.

The reaction temperature can vary widely although it is preferred to maintain the reaction mixture in the liquid phase. Accordingly, typical reaction temperatures will vary from about 20° to about 150° C., preferably from about 40° to about 120° C., and most preferably from about 50° to about 90° C. The reaction pressure is not critical and can be atmospheric, sub-atmospheric or super-atmospheric.

Typically, the reaction pressure is controlled in a manner sufficient to keep the reactants and Co-catalyst II in a liquid phase. Furthermore, it is highly desirable to conduct the reaction under the autogeneous pressure generated by the reactants at the temperature selected.

The process may be run in a batch mode or a stepwise mode or a continuous mode where either one or both the olefin or hydrogen peroxide may be added simultaneously or sequentially to maintain reactant concentration as they are consumed.

Additionally, the process may be run in either of the aforementioned modes by altering the reaction conditions, and/or, the reactant, solvent, or catalyst concentrations during the course of the reaction. Thus, the process may be run by changing the temperature, pressure, catalyst concentration, hydrogen peroxide concentration or olefin concentration.

The practice of the process of the present invention within the aforenoted reaction times is capable of achieving epoxide yields as high as 100%.

Because the catalyst composition of the present invention greatly increases the rate of the epoxide forming reaction, it becomes economically feasible to remove the epoxide product as fast as it is formed by, for example, a product flash-off technique. This permits immediate removal of the epoxide product and substantially reduces the chances for undesirable hydrolysis reaction of the epoxide to corresponding glycol to occur. Thus, a volatile epoxide may be removed by vaporization from the reaction medium preferably by use of a stripping gas. Alternatively, volatile and non-volatile epoxides may also be removed by preferential extraction into a separate solvent phase which then in turn may be removed from the reaction medium preferably by decanting. The reaction mixture from which products and by-products have been removed can be recycled for further use in epoxidizing olefins.

Further isolation of the resulting epoxide from volatilized constituents of the reaction medium or from the extraction medium can be accomplished by fractional distillation to yield the substantially pure epoxide in cases where the epoxide is relatively low boiling.

It is to be understood that while the Group V element containing compounds and phenolic compounds are referred to herein generally as co-catalysts, the exact mechanistic relationship by which these classes of compounds exert their reaction rate reducing effect is not entirely understood. Consequently, the use of the term "co-catalyst" is meant to include the possibility of a promoter/catalyst type of relationship between each of these respective classes of compounds.

The utilities of the epoxidized products produced in accordance with the process of the present invention are well known and include use as intermediates in the preparation of polyesters, polyurethanes, detergent products, and the like.

As used herein, percent epoxide selectivity is defined as:

$$\text{selectivity (\%)} = \frac{\text{moles of epoxide produced}}{\text{moles of H}_2\text{O}_2 \text{ converted to organic products}} \times 100$$

To determine selectivity to by-product, the moles of epoxide in the above equation is replaced by moles of by-product.

Conversion is reported in two forms, namely, conversion of $H_2O_2$ to organic products and total conversion of $H_2O_2$ including organic products as well as decomposition products of $H_2O_2$ such as oxygen and water. Total conversion is determined as follows:

$$\text{Total conversion (\%)} = \frac{\text{moles of H}_2\text{O}_2 \text{ reacted}}{\text{moles of H}_2\text{O}_2 \text{ charged}}$$

Conversion to oragnics is determined as follows:

$$\text{Conversion to organics (\%)} = \frac{\text{moles of H}_2\text{O}_2 \text{ reacted to form organic products}}{\text{moles of H}_2\text{O}_2 \text{ charged}}$$

Unless otherwise specified, total conversion is determined by iodometric titration of residual peroxide remaining after reaction, and conversion to organics is determined by gas chromatography. Most of the conversions disclosed herein are reported as being determined by two different analytical methods because, as is well known, the use of unpassivated stainless steel reactors cause decomposition of hydrogen peroxide (see for example, "Hydrogen Peroxide" by Schumb, W., Satterfield, R., and Wentworth, R., American Chemical Society Monograph, published by Reinhold (1955)). This decomposition of hydrogen peroxide can be eliminated or minimized to a negligible degree by passivating the stainless steel using conventional techniques such as treatment with nitric acid. Consequently, for practical purposes the advantages of the present invention are observed from conversion to organic products and selectivity of these organic products to epoxide. Total conversion is reported herein in the interest of completeness but has no real bearing on the performance of the process of the present invention. The yield of epoxide can be calculated as the product of conversion to organics and selectivity. It is to be noted that the analytical methods for determining total % conversion is associated with between about a ±2 and 4% experimental error, and the analytical method for determining % conversion to organics is associated with about a ±5% experimental error. The above experimental errors are believed to account for those data reported herein where % conversion to organics is higher than total % conversion.

The following examples are given as specific illustrations of the claimed invention. It should be understood, however, that the invention is not limited to the specific details set forth in the examples. All parts and percentages in the examples as well as in the remainder of the specification are by weight unless otherwise specified. Unless otherwise specified, all reactions reported herein below are conducted in a manner such that olefin is available for reaction with $H_2O_2$ in an amount in excess of the stoichiometric amount relative to the $H_2O_2$. Furthermore, while the following examples may be written in the present tense it is to be understood that such examples represent work actually performed.

For purposes of background, publications which report $pK_a$ values of numerous compounds include "Transactions of the Faraday Soc." Vol. 65, p. 1004 (1969) by Rochester and Rossoll; "Ionization Constants of Acids and Bases" by Albert and Serjeant, published by Methuen, N.Y. (1962); "Handbook of Biochemistry", p. J-150 to J-189 C.R.C. Press, Cleveland (1968); "Handbook of Proton Ionization Heats", By Cristensen et al, Wiley Press (1976); "Ionization Constants of Organic Acids in Aqueous Solution" by Serjeant and Dempsey, Pergamon Press (1979); and "A Comparison of the Acid Ionization Constants of Para-t-butyl Phenol, Ortho-t-butyl Phenol, and 2,4-di-t-butyl Phenol in Water and Methanol", J. Chem. Soc., p. 4603 (1965).

EXAMPLE 1

Runs 1 to 8 and 11 of this example are conducted by adding a Co-catalyst I, Co-catalyst II, solvent, an aqueous hydrogen peroxide solution having 40% $H_2O_2$ dissolved therein to a 300 cc, 316 stainless autoclave equipped with a stirrer and the contents mixed together at ambient temperature. The mixture is then heated to a reaction temperature of 70° C. and about 50 g of propylene is fed to the autoclave under a back pressure of 500 to 600 psig of $N_2$ to liquefy the olefin and drive it into solution. Samples are withdrawn and analyzed for residual $H_2O_2$ by iodometric titration and for epoxide by gas chromatography.

The amount and identity of the components of the reaction mixture for each run are summarized at Table I runs 1 to 8 and 11 as are the results obtained therefrom.

COMPARATIVE EXAMPLE 1

Example 1 is repeated for runs 9, 10, and 12 of this Comparative Example with the exception that Co-catalyst II possesses a $pK_a$ above 13 for runs 9 and 12 and Co-catalyst I is omitted for run 10 employing phenol as Co-catalyst II. The results, amounts and identity of the reaction mixture are summarized at Table I.

EXAMPLE 2

This example illustrates the affect of employing diphenyl arsinic acid as co-catalyst I but in much lower amounts than employed in Example 1.

Accordingly, for each run, Co-catalyst I, Co-catalyst II, solvent, and a 40%, by weight, solution of $H_2O_2$ in water, are introduced at ambient temperature into a 125 cc, 316 stainless steel, Parr autoclave fitted with a thermocouple, propylene-feed and vent lines. The resulting reaction mixture is stirred with a stirring magnet. While stirring, the reaction mixture is heated to 70° C. and maintained thereat while propylene is charged to the autoclave to a pressure between 100 and 150 psig. Samples are removed after 60 minutes reaction time and analyzed by iodometric titration and gas chromatography. The results are summarized at Table II, Runs 13 to 29.

COMPARATIVE EXAMPLE 2

Following the general procedures of Example 2, the epoxidation reaction is conducted using the components recited at Table II Run 30. This run omits Co-catalyst I and results in no conversion to organics and no selectivity to epoxide.

EXAMPLE 3

In general accordance with the procedures of Example 1, the epoxidation reaction is conducted using the ingredients and amounts thereof recited in Table III, Runs 31 to 45, as well as a nitrogen back pressure to liquify about 50 g of propylene, the total pressure in the reaction vessel being summarized at Table III for each run. Runs 31 to 35 employ mixtures of Co-catalyst II. Runs 43 to 45 successively recycle the reaction mixture of Co-catalysts I and II from Run 42 after removal of organic conversion products by distillation at reduced pressure, addition of $H_2O_2$ in amounts employed in Run 42, and repressurizing the reactor for each run with propylene. The results are summarized at Table III.

TABLE I

EPOXIDATION OF PROPYLENE at 70° C.

| Run No. | CO-CAT.I Type | Wt. (g) | Moles | CO-CAT.II Type | Wt. (g) | Moles | pKa | SOLVENT Type | Wt. (g) | Aq. 40% $H_2O_2$ sol. (g) | Reaction Time (min.) | CONVERSION (%) Total | To Organics | SELECTIVITY (%) To PO | To PG |
|---|---|---|---|---|---|---|---|---|---|---|---|---|---|---|---|
| 1 | DPAA | 1.26 | .0048 | p-cresol | 75.0 | 0.69 | 10.2 | B | 3.9 | 5.48 | 55 | 100 | 53.1 | 99.2 | 0.8 |
| 2 | " | 1.26 | " | 2,4-di-t-butyl phenol | 75.2 | 0.32 | 11.6 | B | 8.1 | 5.58 | 35 | 90 | 29.1 | 100 | 0 |
| 3 | DPAA | 1.26 | " | p-chlorophenol | 66.9 | 0.52 | 9.2 | B | 11.45 | 5.59 | 29 | 94 | 96.7 | 100 | 0 |
| 4 | " | 1.25 | " | 2-methoxyphenol | 72.7 | 0.59 | 10.0 | B | 3.9 | 5.60 | 55 | 68 | 41.8 | 96.7 | 3.3 |
| 5 | " | 1.25 | " | o-chlorophenol | 70.5 | 0.55 | 8.5 | B | 4.8 | 5.58 | 30 | 79 | 63.9 | 100 | 0 |
| 6 | " | 1.26 | " | m-chlorophenol | 69.8 | 0.54 | 8.8 | B | 4.8 | 5.53 | 30 | 98 | 100 | 100 | 0 |
| 7 | " | 1.25 | " | p-chlorophenol | 66.3 | 0.52 | 9.2 | T | 11.9 | 5.57 | 33 | 96 | 66.1 | 100 | 0 |
| 8 | " | 1.25 | " | p-chlorophenol | 67.4 | 0.53 | 9.2 | B | 11.5 | 5.63 | 45 | 98 | 96.5 | 100 | |
| 9 (Comp) | PAA | 0.97 | " | 2-propanol | 75.0 | 1.39 | 18.0 | None | 0 | 5.49 | 360 | 22 | 9.3 | 89.2 | 10.8 |
| 10 (Comp) | None | 0 | " | phenol | 66.0 | 0.70 | 9.9 | B | 11.4 | 5.62 | 60 | 19 | 14.9 | 100 | 0 |
| 11 | DPAA | 1.26 | " | phenol | 66.1 | 0.70 | 9.9 | B | 11.4 | 5.60 | 60 | 99 | 78.5 | 100 | 0 |
| 12 (Comp) | DPAA | 1.26 | " | 1,4-dioxane | 75.3 | 0.85 | * | None | N/A | N/A | 45 | 33 | 0 | 0 | 0 |

DPAA = diphenylarsinic acid
PAA = phenylarsonic acid
B = benzene
T = toluene
PO = propylene oxide
PG = propylene glycol
N/A = not applicable
*1,4-dioxane is basic

TABLE II

EPOXIDATION OF PROPYLENE AT 70° C., 100 to 150 psig, AND 60 MIN. REACTION TIME

| Run No. | CO-CAT. I[a] Type | Wt. (g) | Moles | CO-CAT. II[b] Type | Wt. (g) | Moles | pKa | SOLVENT[c] Type | Wt. (g) | Aq. 40% $H_2O_2$ sol. (g) | CONVERSION (%) Total | To Organics | SELECTIVITY (%) To PO | To PG |
|---|---|---|---|---|---|---|---|---|---|---|---|---|---|---|
| 13 | DPAA | 0.320 | .0012 | p-CP | 16.76 | 0.13 | 9.2 | BN | 14.94 | 3.93 | 29 | 23 | 99.5 | 0.5 |
| 14 | DPAA | 0.317 | .0012 | p-CP | 20.55 | 0.16 | 9.2 | DMP | 17.74 | 3.48 | 25 | 21 | 99.5 | 0.5 |
| 15 | " | 0.358 | .0014 | p-CP | 21.66 | 0.17 | 9.2 | o-DCB | 19.19 | 3.62 | 79 | 42 | 98.0 | 2.0 |
| 16 | " | 0.326 | .0012 | p-CP | 16.33 | 0.13 | 9.2 | 1-PN | 12.49 | 3.94 | 55 | 37 | 98.0 | 2.0 |
| 17 | " | 0.328 | .0013 | p-CP | 18.40 | 0.14 | 9.2 | EB | 15.66 | 3.63 | 28 | 20 | 96.0 | 4.0 |
| 18 | " | 0.324 | .0012 | p-CP | 18.72 | 0.14 | 9.2 | p-CT | 16.77 | 3.73 | 79 | 21 | 93.0 | 7.0 |
| 19 | " | 0.323 | .0012 | p-CP | 19.59 | 0.15 | 9.2 | NB | 17.29 | 3.85 | 62 | 43 | 99.0 | 1.0 |
| 20 | " | 0.328 | .0013 | p-CP | 19.06 | 0.15 | 9.2 | AN | 13.55 | 3.73 | 18 | 10 | 100 | 0 |
| 21 | " | 0.325 | .0012 | p-CP | 18.43 | 0.14 | 9.2 | DMS | 15.43 | 3.82 | 22 | 18 | 100 | 0 |
| 22 | " | 0.324 | .0012 | 2,4-DCP | 41.19 | 0.25 | 7.7 | None | None | 3.57 | 56 | 35 | 99.8 | 0.2 |
| 23 | " | 0.311 | .0012 | 2,4-DCP | 18.97 | 0.12 | 7.7 | TG | 16.32 | 3.74 | 7 | 4 | 99.1 | 0.9 |
| 24 | " | 0.318 | .0012 | p-CP | 17.16 | 0.13 | 9.2 | EA | 15.63 | 3.70 | 23 | 11 | 99.9 | 0.1 |
| 25 | " | 0.307 | .0012 | p-CP | 17.04 | 0.13 | 9.2 | B | 13.17 | 3.81 | 57 | 39 | 99.3 | 0.7 |
| 26 | " | 0.312 | .0012 | p-CP | 18.97 | 0.15 | 9.2 | BA | 13.33 | 3.98 | 17 | 14 | 100 | 0 |
| 27 | " | 0.324 | .0012 | MIX-P | 42.0 | N/A | N/A | None | None | 3.60 | 83 | 52 | 99.9 | 0.1 |
| 28 | " | 0.326 | .0012 | p-CP | 16.70 | 0.13 | 9.2 | t-butanol | 13.19 | 4.01 | 18 | 4 | 99.9 | 0.1 |
| 29 | " | 0.319 | .0012 | p-CP | 18.03 | 0.14 | 9.2 | tri-n-BP | 14.23 | 3.69 | 35 | 6 | 86.5 | 13.5 |
| 30 (Comp) | " | 0 | 0 | p-CP | 43.29 | 0.33 | 9.2 | toluene | 3.79 | 4.16 | 23 | 0 | 0 | 0 |

[a] DPAA = diphenylarsinic acid
[b] p-CP = p-chlorophenol
2,4-DCP = 2,4-dichlorophenol
MIX-P = Mixture of phenols comprising
 49.8% p-CP
 35.6% o-chlorophenol
 13.1% 2,4-DCP
 0.7% 2,6-dichlorophenol
 0.8% phenol
 (for Pk$_a$'s of each component in mixture see other runs)
[c] BN = benzonitrile
DMP = dimethyl phthalate
o-DCB = o-dichlorobenzene
1-PN = 1-phenylnonane
EB = ethylbenzoate
p-CT = p-chlorotoluene
NB = nitrobenzene
AN = adiponitrile
DMS = dimethylsuccinate
TG = tetraglyme
EA = ethylacetate
B = benzene
BA = butylacetate
tri-n-BP = tri-n-butylphosphate
N/A = not applicable

TABLE III

| Run No. | Co. Cat. I[a] Type | Wt. (g) | Co. Cat. II[b] Type | Wt. (g) | pKa | Benzene Solvent (g) | Aq. 40% $H_2O_2$ sol. (g) | Reaction Pressure (psig) | Temp. (°C.) | Time (min.) | Conversion (%) Total | To Organics | Selectivity % PO | PG |
|---|---|---|---|---|---|---|---|---|---|---|---|---|---|---|
| 31 | DPAA | 1.2579 | 2,4-DCP | 58.35 | 7.7 | 8.208 | 5.433 | 520 | 70 | 50 | N.D. | 89.0 | 89.5 | 10.5 |
|  |  |  | 2,6-DCP | 4.63 | 6.8 |  |  |  |  |  |  |  |  |  |
|  |  |  | 2,4,6-TCP | 2.11 | 7.4 |  |  |  |  |  |  |  |  |  |
| 32 | DPAA | 1.2587 | 2,4-DCP | 46.56 | " | 22.307 | 5.527 | 560 | 70 | 60 | 90.7 | 100 | 77.2 | 22.8 |
|  |  |  | 2,6-DCP | 3.69 |  |  |  |  |  |  |  |  |  |  |
|  |  |  | 2,4,6-TCP | 1.69 |  |  |  |  |  |  |  |  |  |  |
| 33 | DPAA | 1.2564 | 2,4-DCP | 33.28 | " | 37.36 | 5.432 | 520 | 70 | 66 | 82.1 | 86.8 | 58.8 | 41.2 |
|  |  |  | 2,6-DCP | 2.64 |  |  |  |  |  |  |  |  |  |  |
|  |  |  | 2,4,6-TCP | 1.20 |  |  |  |  |  |  |  |  |  |  |
| 34 | DPAA | 1.2594 | 2,4-DCP | 43.67 | " | 8.201 | 5.506 | 560 | 70 | 60 | 93.4 | 89.4 | 72.0 | 28.0 |
|  |  |  | 2,6-DCP | 3.46 |  |  |  |  |  |  |  |  |  |  |
|  |  |  | 2,4,6-TCP | 17.94 |  |  |  |  |  |  |  |  |  |  |
| 35 | DPAA | 1.2601 | 2,4-DCP | 29.83 | " | 8.335 | 5.564 | 580 | 70 | 60 | 91.5 | 93.7 | 61.7 | 38.3 |
|  |  |  | 2,6-DCP | 2.37 |  |  |  |  |  |  |  |  |  |  |
|  |  |  | 2,4,6-TCP | 33.66 |  |  |  |  |  |  |  |  |  |  |
| 36 | DPAA | 1.2591 | p-CP | 66.90 | 9.2 | 11.445 | 5.590 | 530 | 70 | 51 | 100 | 100 | 100 | 0 |
| 37 | DPAA | 1.2550 | p-CP | 36.50 | 9.2 | 37.23 | 5.501 | 580 | 70 | 62 | 91.4 | 95.3 | 93.8 | 6.2 |
| 38 | DPAA | 1.2565 | 2,4-DCP | 71.21 | 7.7 | 4.045 | 5.58 | 560 | 70 | 60 | 96.3 | 100 | 98.0 | 2.0 |
| 39 | DPAA | 1.2525 | 2,4-DCP | 66.69 | " | 8.084 | 5.440 | 550 | 90 | 45 | 98.5 | 86.7 | 96.3 | 3.7 |
| 40 | DPAA | 1.2615 | 2,4-DCP | 65.99 | " | 8.305 | 5.510 | 610 | 90 | 32 | N.D. | 100 | 92.9 | 7.1 |
| 41 | DPAA | 1.2611 | 2,4-DCP | 65.64 | " | 8.024 | 5.410 | 760 | 110 | 25 | N.D. | 100 | 86.2 | 13.8 |
| 42 | DPAA | 1.2513 | 2,4-DCP | 64.63 | " | 8.103 | 5.330 | 610 | 70 | 70 | N.D. | 96.3 | 97.1 | 2.9 |
| 43 | DPAA | R | 2,4-DCP | 62.69 | " | 7.854 | 5.030 | 510 | 70 | 71 | N.D. | 89.3 | 90.4 | 9.6 |
| 44 | DPAA | R | 2,4-DCP | 58.70 | " | 7.465 | 4.650 | 560 | 70 | 70 | N.D. | 100 | 83.4 | 16.6 |

TABLE III-continued

| Run No. | Co. Cat. I[a] Type | Wt. (g) | Co. Cat. II[b] Type | Wt. (g) | pKa | Benzene Solvent (g) | Aq. 40% H₂O₂ sol. (g) | Reaction Pressure (psig) | Temp. (°C.) | Time (min.) | Conversion (%) Total | To Organics | Selectivity % PO | PG |
|---|---|---|---|---|---|---|---|---|---|---|---|---|---|---|
| 45 | DPAA | R | 2,4-DCP | 56.38 | " | 7.326 | 4.330 | 590 | 70 | 71 | N.D. | 100 | 80.0 | 20.0 |

[a]DPAA = diphenylarsinic acid
[b]2,4-DCP = 2,4-dichlorophenol
2,6-DCP = 2,6-dichlorophenol
2,4,6-TCP = 2,4,6-trichlorophenol
p-CP = p-chlorophenol
[c]PO = propylene oxide; PG = propylene glycol
R = recycle
N.D. = not determined

Discussion of Results

Referring to Table 1, Runs 1 to 8 and 11 illustrate a general trend of higher conversion to organics and higher selectivity to epoxide as the $pK_a$ of Co-catalyst II decreases.

Run 9 which uses 2-propanol ($pK_a = 18$) as Co-catalyst II and phenyl arsonic acid as Co-catalyst I results in a conversion to organics of only 9.3%, while the use of 1,4-dioxane, which is basic, results in no conversion to organics or selectivity to epoxide.

Comparing Run 10 with Run 11, the absence of Co-catalyst I in Run 10 results in a reduction in conversion from about 78% to about 15%. Thus, the combination of Co-catalysts I and II are critical to the present invention.

Referring to Table II, the lower amount of Co-catalyst I relative to the Runs of Table I, while resulting in a reduction of conversion to organics, still provides high selectivity to epoxide. Run 30 illustrates the affect of omitting Co-catalyst I altogether, i.e., 0% conversion to organics. The use of a mixture of Co-catalysts II in Run 27 results in an overall increase in conversion to organics.

Referring to Table III, the effect of employing a mixture of Co-catalysts II is further illustrated in Runs 31 to 35. Runs 42 to 45 illustrate that high conversions to organics and selectivity to epoxide are obtainable when the Co-catalyst I and II mixture is continuously recycled over several runs, substantiating the oxidative stability of the halogenated phenols.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for epoxidizing at least one olefinic compound having at least one ethylenic unsaturation which comprises contacting said olefinic compound with hydrogen peroxide in the presence of a catalyst composition comprising at least one Co-catalyst I and at least one Co-catalyst II, in a manner and under conditions sufficient to oxidize at least one of said ethylenically unsaturated groups to its corresponding epoxide group, and wherein said catalyst composition:
   (i) said Co-catalyst I comprises at least one Group V element containing compound which is capable of catalyzing the oxidation reaction between hydrogen peroxide and the ethylenic unsaturation, said Group V element being selected from As, P, Sb, Bi, and mixtures thereof; and
   (ii) said Co-catalyst II is at least one organic compound having a $pK_a$ of from about 5 to about 13 and at least one hydroxy group substituted on an aromatic ring.

2. The process of claim 1 wherein said Co-catalyst I comprises at least one member selected from the group consisting of:
   (a) at least one inorganic Group V element containing compound selected from the group consisting of oxides, oxy acids, alkali metal oxy acid salts, alkaline earth metal oxy acid salts, halides, oxyhalides, thiohalides, sulfides, oxysulfides and metalides; and
   (b) at least one organic Group V element containing compound represented by structural formula selected from the group consisting of:

$R_1 Z X' Y$ $R_1 R_2 Z X'$ $R_1 R_2 R_3 Z$ $R_1 Z_1 (O) X' Y$ $R_1 R_2 Z_1 (O) X'$ and $R_1 R_2 R_3 Z_1 (O)$ wherein: $R_1$, $R_2$, and $R_3$, which may be the same or different are hydrocarbyl groups selected from the group consisting of: unsubstituted alkyl of from about 1 to about 20 carbons, unsubstituted aryl of from about 6 to about 14 carbons, unsubstituted alkoxy, aryloxy, alkoxyaryl, aryloxyalkyl, aralkyl, alkylthio, arylthio, and alkaryl wherein the alkyl and aryl groups thereof are as described immediately above in connection with alkyl and aryl respectively, unsubstituted cycloalkyl of from about 4 to about 20 carbons, or any two of said $R_1$, $R_2$, and $R_3$ groups together can constitute a cyclic hydrocarbon group having from about 4 to about 20 carbons; substituted: alkyl, aryl, alkoxy, aryloxy, alkoxyaryl, aryloxyalkyl, alkaryl, alkylthio, arylthio, aralkyl, and cycloalkyl, said substituted hydrocarbyl groups being as defined immediately above in connection with the unsubstituted hydrocarbyl groups and said substituents being selected from the group consisting of halogen, nitro, and mixtures thereof: and wherein X' and Y, which may be the same or different, are selected from the group consisting of hydrogen, halogen, hydroxy, the hydrocarbyl groups of alkyl, aryl, alkaryl, aralkyl, and alkoxy said hydrocarbyl groups being defined in connection with $R_{1 \text{ to } 3}$ above, mercapto, acyloxy of the structural formula

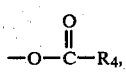

alkylthio of the structural formula $-SR_5$, and thioacyloxy of the structural formula

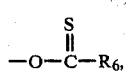

wherein $R_4$, $R_5$, and $R_6$ are independently alkyl of from about 1 to about 20 carbons; Z represents one of said Group V elements in the plus 3 oxidation state; and Z' represents one of said Group V elements in the plus 5 oxidation state.

3. The process of claim 2 wherein Co-catalyst I comprises at least one compound represented by the structural formula:

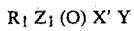

wherein X' and Y are hydroxy, $R_1$ is a halogen substituted or unsubstituted hydrocarbyl group selected from the group consisting of alkyl, aryl, aralkyl, and alkoxyaryl as defined in connection with $R_1$, and $Z_1$ represents said Group V element in the plus 5 oxidation state.

4. The process of claim 1 wherein Co-catalyst I comprises at least one compound represented by the structural formula

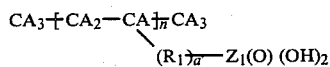

wherein $Z_1$ represents said Group V element in the plus 5 oxidation state, A is independently selected from the group consisting of hydrogen and halogen, $R_1$ is a hydrocarbyl group selected from the group consisting of alkyl of from about 1 to about 20 carbons, and aryl of from about 6 to about 14 carbons, a' is a number of 0 or 1, and n is a number which can vary from about 5 to about 1000.

5. The process of claim 1 wherein said Co-catalyst II comprises at least one member represented by the structural formula:

wherein Ar represents a substituted or unsubstituted aromatic hydrocarbyl group having from about 6 to about 14 carbons exclusive of substituents, said substituents when present being independently selected from the group consisting of alkyl of from about 1 to about 20 carbons, hydroxyalkyl, halogenated alkyl, nitroalkyl, alkoxyalkyl, aralkoxy, oxy substituted alkyl, alkoxy carbonyl, wherein the respective alkyl and aryl portions thereof are as described immediately above in connection with aryl and alkyl, and said halogen is as described in connection with X below; X represents a member independently selected from the group consisting of hydrogen, nitro, and a halogen selected from Cl, F, Br, and I; the letter "a" represents a number of from 0 to 5; the letter "b" represents a number of at least 1; and the sum of a+b is equal to the total number of available carbon bonding sites on the Ar substituted or unsubstituted hydrocarbyl group.

6. The process of claim 5 wherein X is Cl, "a" is at least 1, and Ar contains 6 carbons exclusive of substituents and said substituents are selected from the group consisting of alkyl, halogenated alkyl, and nitroalkyl.

7. The process of claim 5 wherein Co-catalyst II comprises a compound represented by the structural formula:

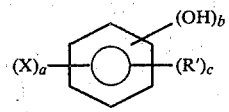

wherein R' is independently selected from the group consisting of alkyl of from about 1 to about 5 carbons, and alkoxy wherein the alkyl portion thereof is as described above; the letter "c" represents a number of from 0 to 5; X, a, and b are as described in claim 5, and the sum of a+b+c is equal to the total number of available carbon bonding sites on the aromatic ring.

8. The process of claim 7 wherein X is chlorine, b=1, c=0 and a=1 to 3.

9. The process of claim 1 wherein Co-catalyst II is selected from at least one member of the group consisting of p-chlorophenol, o-chlorophenol, m-chlorophenol, 2,4-dichlorophenol, 2,6-dichlorophenol, 2,4,6-trichlorophenol, 2,3-dichlorophenol, pentachlorophenol, p-cresol, phenol, 2,3,5-trimethylphenol, 2-methoxyphenol, o-nitrophenol, p-nitrophenol, 2,4-dinitrophenol, 2,4-di-t-butylphenol, and pentamethylphenol.

10. The process of claim 1 wherein Co-catalyst I is selected from the group consisting of phenylarsonic acid, diphenylarsinic acid, 2-nitro-4-methylphenylarsonic acid, 4-methylphenylarsonic acid, n-propylarsonic acid, arsenic triethoxide, and mixtures thereof and Co-catalyst II is selected from the group consisting of o-chlorophenol, m-chlorophenol, p-chlorophenol 2,4-dichlorophenol, 2,6-dichlorophenol, 2,4,6-trichlorophenol and mixtures thereof.

11. The process of any one of claims 1 to 10 wherein said epoxidation reaction is conducted by contacting in the liquid phase said olefin with a liquid reaction mixture comprising:

(a) hydrogen peroxide initially added to said reaction mixture as an aqueous solution, containing from about 20 to about 75%, by weight $H_2O_2$, based on the weight of said solution, in an amount of from about 0.5 to about 25%, by weight, based on the total weight of said reaction mixture exclusive of olefin and Co-catalyst I;

(b) Co-catalyst II in an amount of from about 10 to about 99.5%, by weight, based on the weight of said reaction mixture exclusive of the weight of olefin and Co-catalyst I;

(c) inert organic solvent in an amount of from about 0 to about 90%, by weight, based on the weight of the reaction mixture exclusive of the weight of olefin and Co-catalyst I; and (d) Co-catalyst I in an amount sufficient to achieve from about 0.001 to about 2 g atoms of said Group V element in Co-catalyst I per liter of reaction mixture inclusive of components a through c recited above;

said reaction mixture being maintained at a temperature of from about 20° to about 150° C. and the contacting of said olefin with said reaction mixture being conducted in a manner sufficient to achieve an initial molar ratio of olefin to $H_2O_2$ present in said reaction mixture of from about 0.8:1 to about 50:1.

12. The process of claim 11 wherein: the hydrogen peroxide is initially added to the reaction mixture as an aqueous solution containing from about 20 to about 45% $H_2O_2$ and the $H_2O_2$ is present in said reaction mixture in an amount of from about 2 to about 20%, by weight, thereof, exclusive of the weight of olefin and Co-catalyst I; Co-catalyst II is present in said reaction mixture in an amount of from about 30 to about 90%, by weight thereof, exclusive of the weight of olefin and Co-catalyst I; the inert organic solvent is selected from the group consisting of benzene, toluene, xylene, pentane, hexane, heptane, isopropanol, acetone, propanoic acid, ethyl acetate, ethyl benzoate, dimethyl succinate, dimethyl phthalate, tetraglyme, nitrobenzene, benzonitrile and mixtures thereof and is present in said reaction mixture in an amount of from about 0 to 50%, by weight thereof, based on the weight of the reaction mixture exclusive of the weight of olefin and Co-catalyst I; and Co-catalyst I is present in said reaction mixture in an amount sufficient to achieve from about 0.005 to about 1 g atom of the Group V element of Co-catalyst I per liter of reaction mixture inclusive of components a through d, and wherein the initial molar ratio of olefin to $H_2O_2$ present in said reaction mixture is from about 1:1 to about 30:1.

13. A process for epoxidizing an olefin selected from the group consisting of ethylene and propylene and mixtures thereof with $H_2O_2$ which comprises contacting, in the liquid phase, said olefin with a reaction mixture in a manner and under conditions sufficient to form a product selected from the group consisting of ethylene oxide, propylene oxide, and mixtures thereof, said reaction mixture comprising:
(a) hydrogen peroxide, initially added to the reaction mixture as an aqueous solution containing from about 20 to about 75% by weight $H_2O_2$, based on the weight of said solution, in an amount of from about 10 to about 15%, by weight based on the weight of the reaction mixture exclusive of the weight of olefin and Co-catalyst I;
(b) as a Co-catalyst II, p-chlorophenol in an amount of from about 30 to about 90%, by weight, based on the weight of the reaction mixture exclusive of the weight of olefin and Co-catalyst I; and
(c) at least one Co-catalyst I selected from the group consisting of phenylarsonic acid, diphenylarsinic acid, 4-hydroxy-3-nitrophenyl arsonic acid, and mixtures thereof, in an amount sufficient to achieve from about 0.01 to about 1 g atom of arsenic per liter of reaction mixture inclusive of components a and b.

* * * * *